United States Patent [19]

Suzuki et al.

[11] Patent Number: 4,673,692

[45] Date of Patent: Jun. 16, 1987

[54] DIPHENYLMETHYLIMINE DERIVATIVES, THEIR COMPOSITIONS AND PHARMACEUTICAL USES

[75] Inventors: Yasushi Suzuki, Yokohama; Yukio Hasegawa, Yamato; Michitaka Sato, Kawasaki; Morinobu Saito, Kawasaki; Norio Yamamoto, Kawasaki; Katsuhiko Miyasaka, Atsugi; Takashi Mikami, Yokohama; Katsuhiko Miyazawa, Kawasaki, all of Japan

[73] Assignee: Teikoku Hormone Mfg. Co., Ltd., Tokyo, Japan

[21] Appl. No.: 789,275

[22] Filed: Oct. 18, 1985

[30] Foreign Application Priority Data

Oct. 19, 1984 [JP] Japan .............................. 59-218679

[51] Int. Cl.[4] .................... A61K 31/175; A61K 31/15; C07C 131/00
[52] U.S. Cl. .................................. 514/583; 514/590; 514/614; 514/639; 514/640; 564/20; 564/36; 564/251; 564/254; 564/266
[58] Field of Search ............... 564/251, 254, 266, 259, 564/20, 36, 192; 514/639, 640, 583, 590, 614

[56] References Cited

U.S. PATENT DOCUMENTS 3,925,472 12/1975 Swanson .............................. 564/266
4,124,725 11/1978 Moore ................................. 514/646

OTHER PUBLICATIONS

Clark, N. G. Modern Organic Chemistry (1964) Oxford University Press, p. 185.
Robert W. Kreilick, Journal of the American Chemical Society, Nov. 20, 1966, pp. 5284–5288.

Primary Examiner—Natalie Trousof
Assistant Examiner—L. Hendriksen

[57] ABSTRACT

A compound represented by the formula

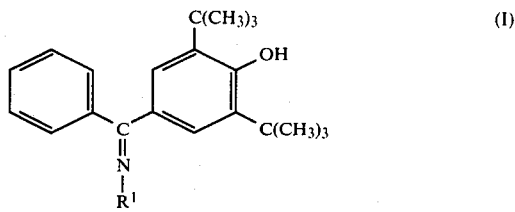

wherein $R^1$ represents a hydroxyl group, an alkanoyloxy group or a group of the formula

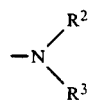

in which $R^2$ represents a hydrogen atom or a lower alkyl group, and $R^3$ represents a hydrogen atom, a lower alkyl group, an alkanoyl group, a phenyl group, a carbamoyl group or a thiocarbamoyl group, or a salt thereof.

The said compound can be prepared by reacting a compound represented by the formula

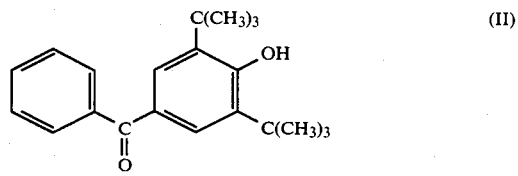

with a compound of the formula $$NH_2-R^1 \qquad (III)$$

wherein $R^1$ is as defined hereinabove, or a salt thereof, and as required, alkanoylating the resulting compound of formula (I) in which $R^1$ represents a hydroxyl group or an amino group, and as required, converting the resulting compound of formula (I) in which $R^1$ is the group

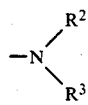

into its salt, and is useful for the treatment of inflammation, pain or rheumatism.

7 Claims, No Drawings

DIPHENYLMETHYLIMINE DERIVATIVES, THEIR COMPOSITIONS AND PHARMACEUTICAL USES

This invention relates to novel diphenylmethylimine derivatives. More specifically, it relates to compounds represented by the following formula

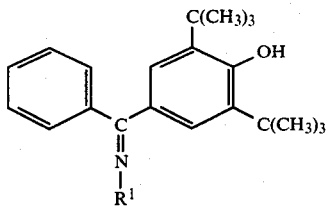

wherein $R^1$ represents a hydroxyl group, an alkanoyloxy group or a group of the formula

in which $R^2$ represents a hydrogen atom or a lower alkyl group, and $R^3$ represents a hydrogen atom, a lower alkyl group, an alkanoyl group, a phenyl group, a carbamoyl group or a thiocarbamoyl group, or salts thereof, a process for production thereof, and the use of the aforesaid compounds or salts as drugs, particularly as anti-inflammatory, analgesic and anti-rheumatic agents.

With regard to diphenylmethylimine derivatives, a compound of the following formula

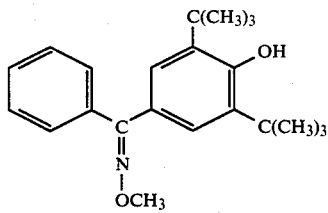

, for example, was previously disclosed [see Robert W. Kreilick, J. Am. Chem. Soc., 88, 5284, 1966)], but this paper fails to describe anything about the utility of this compound. The present inventors synthesized this compound and examined its pharmacological actions. The results led to the confirmation that the above compound does not substantially show pharmacological actions such as anti-inflammatory, analgesic or anti-rheumatic activity.

U.S. Pat. No. 4,124,725 discloses that benzophenone derivatives of the following formula

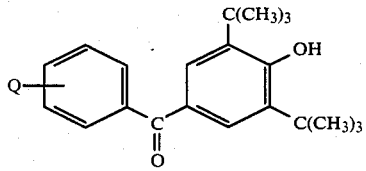

wherein Q represents a hydrogen atom, a 2- or 4-fluoro group, an alkoxy group having 1 to 3 carbon atoms, a hydroxyl group, an amino group or a methylthio group, have anti-inflammatory activity. These benzophenone derivatives, however, have the serious defect that as is the case with conventional analgesic, anti-inflammatory agents such as aspirin, phenylbutazone and indomethacine which have gained widespread use, they induce a fairly great trouble in the digestive organs.

The present inventors have now found that the diphenylmethylimine derivatives of formula (I) given above have the excellent action of inhibiting cyclooxygenase and lipoxygenase of polyunsaturated fatty acids, particularly arachidonic acid, which are considered to be much involved in inflammatory reactions of animal organisms and hardly induce troubles in the digestive organs, and are expected to be useful anti-inflammatory, analgesic and anti-rheumatic agents with little gastrointestinal troubles.

The present inventors have also found that the diphenylmethylimine derivatives of formula (I) have antioxidant activity.

The term "lower", used throughout the present specification and claims, means that an atomic grouping or a compound qualified by this term has not more than 6, preferably not more than 4, carbon atoms.

The "lower alkyl group", as used in the present specification and claims, means a linear or branched monovalent lower saturated aliphatic hydrocarbon group, and includes, for example, methyl, ethyl, n-propyl, isopropyl, n-butyl, sec-butyl, isobutyl, tert-butyl and n-pentyl groups.

The "alkanoyloxy group" and the "alkanoyl group", as used in the present specification and claims, mean groups of the formulae

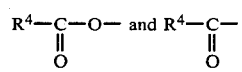

wherein $R^4$ represents an alkyl group. The alkyl group represented by $R^4$ may be linear or branched, and specifically includes, for example, methyl, ethyl, n-propyl, isopropyl, n-butyl, sec-butyl, isobutyl, tert-butyl, n-pentyl, isopentyl, n-hexyl, n-heptyl, n-octyl, and 2-ethylhexyl groups. Alkyl groups having not more than 10 carbon atoms, particularly lower alkyl groups, are preferred.

Examples of the alkanoyl moiety

in the "alkanoyloxy group" and the "alkanoyl group" include acetyl, propionyl, butyryl, isobutyryl, valeryl and octanoyl groups.

Examples of the "group of the formula

include amino, methylamino, ethylamino, dimethylamino, diethylamino, acetylamino, propionylamino, butyrylamino, N-acetyl-N-methylamino, phenylamino, N-methyl-N-phenylamino, ureido, thioureido, 1-methylureido and 1-methylthioureido groups.

Typical examples of the compound of formula (I) provided by this invention are:

3,5-di-t-butyl-4-hydroxybenzophenone oxime,
3,5-di-t-butyl-4-hydroxybenzophenone O-acetyloxime,
3,5-di-t-butyl-4-hydroxybenzophenone O-propionyloxime,
3,5-di-t-butyl-4-hydroxybenzophenone O-butyryloxime,
3,5-di-t-butyl-4-hydroxybenzophenone O-isobutyryloxime,
3,5-di-t-butyl-4-hydroxybenzophenone O-valeryloxime,
3,5-di-t-butyl-4-hydroxybenzophenone O-octanoyloxime,
3,5-di-t-butyl-4-hydroxybenzophenone hydrazone,
3,5-di-t-butyl-4-hydroxybenzophenone methylhydrazone,
3,5-di-t-butyl-4-hydroxybenzophenone dimethylhydrazone,
3,5-di-t-butyl-4-hydroxybenzophenone diethylhydrazone,
3,5-di-b-butyl-4-hydroxybenzophenone acetylhydrazone,
3,5-di-t-butyl-4-hydroxybenzophenone propionylhydrazone,
3,5-di-t-butyl-4-hydroxybenzophenone N-acetyl-N-methylhydrazone,
3,5-di-t-butyl-4-hydroxybenzophenone phenylhydrazone,
3,5-di-t-butyl-4-hydroxybenzophenone N-methyl-N-phenylhydrazone,
3,5-di-t-butyl-4-hydroxybenzophenone semicarbazone,
3,5-di-t-butyl-4-hydroxybenzophenone 2-methylsemicarbazone, and
3,5-di-t-butyl-4-hydroxybenzophenone thiosemicarbazone.

Preferred compounds of formula (I) are those in which $R^1$ is a hydroxyl group, an alkanoyloxy group or an amino group, particularly a hydroxyl group or a propionyloxy group.

Compounds of formula (I) in which $R^1$ represents the group $$-N\begin{matrix}R^2\\R^3\end{matrix}$$

may also exist in the form of salts. Examples of such salts are hydrochlorides, sulfates, phosphates, acetates, and succinates. Of these, pharmaceutically acceptable salts are suitable.

The compound of formula (I) includes the two stereoisomers represented by the following formulae.

Z—type (syn-type)

E—type (anti-type)

It should be understood that the compound of formula (I) provided by this invention includes these two stereoisomers and mixtures of these stereoisomers in arbitrary mixing ratios.

According to this invention, the compound of formula (I) or its salt can be produced, for example, by reacting a compound represented by the following formula (II)

with a compound of the formula $$NH_2-R^1 \qquad (III)$$

wherein $R^1$ is as defined hereinabove, or its salts, and as required, alkanoylating the resulting compound of formula (I) in which $R^1$ is a hydroxyl group or an amino group, and as required, converting the resulting compound of formula (I) in which $R^1$ is the group $$-N\begin{matrix}R^2\\R^3\end{matrix}$$

into its salt.

The reaction of the compound of formula (II) with the compound of formula (III) or its salt may be carried out in the absence of a solvent or in the presence of a suitable inert solvent at a temperature of usually about 40° C. to the refluxing temperature of the reaction mixture, preferably at the refluxing temperature of the reaction mixture. Examples of the inert solvent that can be used in this reaction includes alcohols such as methanol, ethanol, propanol and isopropanol, ethers such as dioxane, tetrahydrofuran and dimethoxyethane, aromatic hydrocarbons such as benzene and toluene, organic bases such as pyridine, dimethylaniline, diethylaniline and picoline, water, and mixtures thereof.

The compound of formula (III), for example hydroxylamine, is commercially available usually in the form of a salt. When the compound of formula (III) in the form of a salt is used as a starting material, it is convenient to use the organic base as the solvent, or to carry out the reaction in the presence of an acid binder such as sodium carbonate, potassium carbonate, sodium hydroxide, potassium hydroxide, sodium acetate or potassium acetate while the compound of formula (III) in the form of a salt is being converted to a free compound.

Some of the compounds of formula (III) are available in hydrous form. If such a hydrous compound of formula (III) is used as the starting material, an acid catalyst such as hydrochloric acid, hydrobromic acid, p-toluenesulfonic acid or trifluoroacetic acid can be caused to be present in the reaction system in order to promote the reaction. Even in the absence of the acid catalyst, however, the reaction proceeds sufficiently if the temperature and pressure are elevated.

The proportion of the compound of formula (III) or its salt is not particularly restricted, and can be varied over a wide range. Generally, it is advantageous to use the compound of formula (III) or its salt in a proportion of 1 to 10 moles, preferably 1.5 to 3 moles, per mole of the compound of formula (II).

The compound of formula (I) formed by the above reaction may be isolated from the reaction mixture and purified by methods known per se, such as filtration, extraction, recrystallization and chromatography.

By selecting the solvent and temperature in recrystallization, a mixture of the Z-type stereoisomer of compound (I) and the E-type stereoisomer of compound (I) in an arbitrary ratio can be obtained. For example, by using ethanol as the recrystallization solvent and the recrystallization is carried out at room temperature, the E-type stereoisomer can be obtained. When a mixture of dichloromethane and n-hexane is used as the recrystallization solvent and the recrystallization is carried out at room temperature, the Z-type stereoisomer can be obtained. When the product is dissolved in isopropanol under heat and the solution is poured into water to precipitate crystals, a 50:50 mixture of the E-type and Z-type stereoisomers can be obtained.

The resulting compound of formula (I) in which $R^1$ is a hydroxyl group or an amino group [this compound will be referred to hereinbelow as compound (I-1)] can be converted to a compound of formula (I) in which $R^1$ is an alkanoyloxy or alkanoylamino group [this compound will be referred to hereinbelow as compound (I-2)] by reacting the compound (I-1) with a suitable alkanoylating agent, for example a reactive derivative of $R^4COOH$ (such as an acid halide, acid anhydride, mixed acid anhydride or active ester). The alkanoylation reaction of the compound (I-1) may be carried out by known alkanoylating methods. Specifically, the compound (I-2) can be produced, for example, by reacting the compound (I-1) with a compound of formula $R^4COX$ in which X is a halogen atom and $R^4$ is as defined in a suitable solvent such as pyridine, dimethylaniline, diethylaniline, picoline, chloroform or carbon tetrachloride under ice cooling or at the refluxing temperature of the reaction mixture, preferably at room temperature, optionally in the presence of an acid binder such as sodium carbonate, potassium carbonate, sodium hydroxide or potassium hydroxide.

The diphenylmethylimine derivatives of formula (I) provided by this invention as described hereinabove have strong lipoxygenase and/or cyclooxygenase inhibiting actions, and have very little actions of inducing troubles in the digestive organs. Accordingly, they are particularly useful as a new type of anti-inflammatory, analgesic and anti-rheumatic agents. The compounds of formula (I) in accordance with this invention also exhibit a variety of pharmacological activities, for example antithrombosis, prevention of metastasis and proliferation of tumors, anti-asthma activity, anti-allergic activity, improvement in arteriosclerosis, improvement of atherosclerosis, improvement in the nephrotic, cerebral and cardiovascular systems, and immune regulation, and in addition to anti-inflammatory, analgesic and anti-rheumatic agents, they are also expected to be useful as an anti-asthma agent, an anti-allergic agent (for the prevention and treatment of allergic dermatitis, allergic rhinitis, urticaria, gastrointestinal tract allergy, food allergy and other allergic diseases), an anti-thrombotic agent, an agent for treating arteriosclerosis, an agent for treating vasospasm following subarachnoid hemorrhage, an agent for treating impaired cerebral circulation, an agent for treating coronary insufficiency, an agent for treating ischemic myocardial infarction, an agent for treating ischemic cerebral embolism, an agent for regulating immunity, an agent for treating ulcerative colitis, and an agent for treating psoriasis. The compounds of this invention are also expected to find application as antioxidants.

The excellent pharmacological activities of the compounds of formula (I) provided by this invention are confirmed by the following experiments.

The compounds of this invention used in the following experiments are shown by the following symbols.

Compounds

A: 3,5-di-t-butyl-4-hydroxybenzophenone oxime

B: 3,5-di-t-butyl-4-hydroxybenzophenone O-acetyloxime

C: 3,5-di-t-butyl-4-hydroxybenzophenone O-propionyloxime

D: 3,5-di-t-butyl-4-hydroxybenzophenone hydrazone (1) Anti-inflammatory activity Male Wistar rats weighing 120 to 150 g which had been fasted for 24 hours were used in groups each consisting of 5 rats. In each group, the volumes of the right hind paw were measured by a volume differential meter (made by Ugo Basile Company), and each of the test compounds was suspended in an aqueous solution of 0.5% of carboxymethyl cellulose and 2.0% of Tween 80, and administered orally through a tube. After one hour from the administration, 0.1 of a 1% suspension of carrageenan in distilled water was subcutaneously injected into the plantar tissues of the right hind paw. Three hours later, the volumes of the right hind paw were again measured. The increase in volume of the right hind paw of each rat in each group (the volume of edema) was measured. The percent edema inhibition was calculated in accordance with the following equation, and the results are shown in Tale 1.

TABLE 1

Percent inhibition = (%)

$$\frac{\begin{pmatrix}\text{Average increase} \\ \text{in volume of right} \\ \text{hind paw in the} \\ \text{control group ad-} \\ \text{ministered with} \\ \text{the vehicle}\end{pmatrix} - \begin{pmatrix}\text{Increase in volume} \\ \text{of right hind paw} \\ \text{in each rat in the} \\ \text{groups administered} \\ \text{with the test} \\ \text{compound}\end{pmatrix}}{\begin{pmatrix}\text{Average increase in} \\ \text{volume of right hind} \\ \text{paw in the control} \\ \text{group administered} \\ \text{with the vehicle}\end{pmatrix}} \times 100$$

| Compound | Dosage (mg/kg, p.o.) | Percent inhibition (%) |
|---|---|---|
| A | 10 | 26.7 |
| B | 10 | 22.7 |
| C | 10 | 23.6 |

TABLE 1-continued $$\text{Percent inhibition} = \frac{\begin{pmatrix} \text{Average increase} \\ \text{in volume of right} \\ \text{hind paw in the} \\ \text{control group ad-} \\ \text{ministered with} \\ \text{the vehicle} \end{pmatrix} - \begin{pmatrix} \text{Increase in volume} \\ \text{of right hind paw} \\ \text{in each rat in the} \\ \text{groups administered} \\ \text{with the test} \\ \text{compound} \end{pmatrix}}{\begin{pmatrix} \text{Average increase in} \\ \text{volume of right hind} \\ \text{paw in the control} \\ \text{group administered} \\ \text{with the vehicle} \end{pmatrix}} \times 100$$

| Compound | Dosage (mg/kg, p.o.) | Percent inhibition (%) |
| --- | --- | --- |
| D | 10 | 21.0 |

(2) Lipoxygenase and cyclooxygenase inhibiting actions

The actions of the compounds of this invention to inhibit 5-lipoxygenase and cyclooxygenase activities were measured in accordance with the method of Siegel et al. [Prostaglandins, Vol. 21, page 123 (1981)].

The exudate was extracted from the pleural cavity of a rat with carrageenan-induced pleurisy. White blood cells from the exudate were suspended in 50 mM Tris-HCl buffer (pH 7.4) containing 100 mM sodium chloride and 1 mM calcium chloride. To a fixed amount of the white blood cell suspension were added a test compound, $^{14}C$ arachidonic acid and a calcium ionophore ($A_{23187}$), and the mixture was incubated for 2 minutes. The resulting $^{14}C$ arachidonic acid metabolites were fractionated by thin-layer chromatography (silica gel; plastic plate; developing solvent: hexane/diethyl ether/acetic acid=40/60/2). The thin-layer plate was exposed to an X-ray film, and by comparison with an authentic sample, the individual arachiodonic acid metabolite fractions were identified. The corresponding fractions and other radioactive fractions were collected. The radioactivity of each of the fractions was measured by a liquid scintillation counter, and the percentage of the radioactivity of each fraction based on the total radioactivity was calculated (the ratio of formation). The inhibition ratio of the test compound against the synthesis ability of each fraction was determined by using the ratio of formation as an index.

The lipoxygenase activity was determined by using the formation of 5S-hydroxy-6,8,11,14-eicosatetraenoic acid (5-HETE) and 5S,12R-dihydroxy-6,8,10,14-eicosatetraenoic acid (5,12-diHETE) as indices. The cyclooxygenase activity was determined by using the formation of 12-hydroxyheptadecatrienoic acid (HHT) as an index.

The test compound was used as a solution in dimethyl sulfoxide in a concentration of 10%. The final concentration of dimethyl sulfoxide in the assay system was 2.5%.

The results show that compound A of this invention inhibits 50% of the formation of 5-HETE and 5,12-diHETE in a concentration of 6.2 $\mu M$, and also 50% of the formation of HHT in a concentration of 1.25 $\mu M$.

(3) Preventive effect on adjuvant-induced arthritis

Sprague-Dawley strain female rats, 6 weeks old, were used. Killed and dried M. butyricum (Difco) were suspended (6 mg/ml) in light liquid paraffin, and the suspension was sterilized under pressure to form Freund's complete adjuvant. 0.1 ml of the Freund's complete adjuvant was injected subcutaneously into the right hind paws of the animals to induce arthritis. After the injection of the Freund's complete adjuvant, the test compound was orally administered once a day for 21 consecutive days including the day of injection. The volumes of the left and right hind paws were measured by using the device devised by Fujihira [Eiichi Fujihira: Oyo Yakuri 5, 169–182 (1971)], and the increases in volume from before the injection of the adjuvant was measured and used as an index of swelling. Changes in swelling after the stopping of drug administration were also examined. The animals were used in groups each consisting of 10 members.

It was consequently found that the compound A of this invention significantly ($p<0.05$, $n=10$) inhibited the development of adjuvant-induced arthritis in a dose of at least 3 mg/kg, p.o. No rebound phenomenon was noted in swelling after the stopping of drug administration.

(4) Inhibitory effect on granuloma formation

Wistar strain male rats were used. Under anesthesia with hexobarbital-Na (100 mg/kg, i.p.), the hair of the back of each rat was removed. Filter paper pieces prepared in tablet form (Toyo Filter Paper, No. 85K, 9 mm diameter) sterilized under pressure were implanted subcutaneously on the left and right sides of the back, and oily procaine penicillin G (a product of Banyu Pharmaceutical Co., Ltd.; 300,000 units/ml) was intramuscularly injected in an amount of 0.25 ml.

After the implantation of the filter paper pieces, the test compound was orally administered once a day for 7 consecutive days including the day of implantation. On the day next to the day of the final administration, the filter paper pieces and granuloma formed around them were excised, and dried at about 60° C. for 24 hours. Their weight was measured. The weight of the filter paper pieces was subtracted, and the balance was defined as the dry amount of glanuloma.

It was found that the compound A significantly ($p<0.001$, $n=7-8$) decreased the dry weight of granuloma in a dose of at least 3 mg/kg, p.o.

(5) Ulcerogenic activity

The test compound was orally administered by the same way as in the test on anti-inflammatory activity to male Wistar rats weighing 120 to 150 g which had been fasted for 24 hours. Four hours later, they were killed with ether. Then, the stomach was removed from each rat, and the number of rats whose stomachs showed bleeding at the mucosal membrane and damage beneath the mucosal membrane was counted against the number of animals used.

It was found consequently that the compound A of this invention shows no gastric trouble even when administered in a dose of 300 mg/kg, p.o.

(6) Toxicity

The test compound was suspended in a 10% gum arabic solution, and orally administered to SD-strain male rats (body weight 100–115 g) in 5-membered groups. The animals were observed for 2 weeks. No case of death was observed when the compound A was administered in a dose of 1250 mg/kg.

The compound of formula (I) provided by this invention can be administered orally, parenterally (for example, intramuscularly, intravenously, subcutaneously, or intrarectally), or topically to man and other mammals for the treatment or prevention of various diseases induced by the participation of lipoxygenase and/or cyclooxygenase metabolites.

For use as medicaments, the compound of formula (I) may be formulated into various forms suitable for oral, parenteral or topical administration. For example, the compound of this invention can be formulated by using various nontoxic carriers or diluents normally used in drugs of this type, for example, vehicles, binders, lubricants, disintegrants, antiseptics, isotonizing agents, stabilizers, dispersants, antioxidants, coloring agents, flavoring agents, buffers, propellants and surface-active agents.

Depending upon their uses, such medicaments may be formulated into tablets, capsules, granules, powders, pellets, pills, trouches, suppositories, ointments, patches, injectable preparations, syrups, and aerosols. Specific examples of the nontoxic carriers or diluents which can be used include starch, gelatin, glucose, lactose, fructose, maltose, magnesium carbonate, talc, magnesium stearate, methyl cellulose, carboxymethyl cellulose or its salts, gum arabic, polyethylene glycol, alkyl p-hydroxybenzoates, syrup, ethanol, propylene glycol, Vaseline, carbowax, glycerol, sodium chloride, sodium sulfite, sodium phosphate, citric acid, dichlorodifluoromethane, 1,2-dichlorotetrafluoroethane and sorbitan trioleate.

The medicaments may also contain other therapeutically effective drugs.

The dose of the compound of formula (I) can be varied widely depending upon the type of the animal to be treated, the route of administration, the severity of the condition, the diagnosis of a physician, etc. Generally, it may be 0.1 to 50 mg/kg, preferably 0.2 to 20 mg/kg, per day. It is of course possible to administer the compound of formula (I) in a dose larger than the above-specified upper limit or smaller than the above-specified lower limit according to the severity of the patient's condition and the physician's diagnosis. The above dose may be taken once a day or in several portions a day.

The following examples further illustrate the present invention.

EXAMPLE 1

12.4 g of 3,5-di-t-butyl-4-hydroxybenzophenone and 3.15 g of hydroxylamine hydrochloride were dissolved in 100 ml of ethanol, and with stirring, a solution of 2.77 g of potassium hydroxide in 20 ml of ethanol was added dropwise at room temperature. The mixture was then refluxed for 24 hours with stirring. After cooling, dichloromethane was added to the reaction mixture. The dichloromethane layer was separated, washed with water, and dried. The solvent was distilled off, and n-hexane was added to the residue. The precipitated crystals were collected by filtration, and recrystallized from ether/n-hexane to give 3,5-di-t-butyl-4-hydroxybenzophenone oxime.

Melting point: 150.6°–151.4° C.

NMR, $\delta_{CDCl_3}^{ppm}$: 1.38, 1.43 (18H), 5.34 (1H), 7.26 (2H, s), 7.38 (5H, s), 8.10–8.70 (1H).

IR, $\gamma_{KBr}^{cm-1}$: 3600, 3230, 2950, 1435, 1320, 1240, 770, 700.

EXAMPLE 2

40 g of 3,5-di-t-butyl-4-hydroxybenzophenone and 10.8 g of hydroxylamine hydrochloride were added to 40 ml of pyridine, and the mixture was refluxed for 3 hours. After the reaction, pyridine was distilled off under reduced pressure. The residue was cooled, and then extracted with ethyl acetate. The extract was washed with water and 2N hydrochloric acid, and dried. The solvent was distilled off, and the residue was recrystallized in accordance with the following procedures (a) to (c).

(a) The residue was recrystallized from hydrous isopropanol. The resulting crude crystals were dissolved under heat in 5% hydrous isopropanol (95% isopropanol). The resulting solution was poured into water to obtain a colorless crystalline powder of 3,5-di-t-butyl-4-hydroxybenzophenone oxime. Analysis of the crystals by HPLC (high performance liquid chromatography) showed that the product consisted of a 50:50 mixture of stereoisomers of the E-type and Z-type.

Melting point: 151°–156° C.

NMR, $\delta_{CDCl_3}^{ppm}$: 1.38, 1.43 (18H), 5.34 (1H), 7.24, 7.28 (2H), 7.25–7.55 (5H, m).

IR, $\gamma_{KBr}^{cm-1}$: 3624, 3284, 2964, 1442, 1320, 1240, 1162, 776, 706.

(b) The residue was recrystallized from ethanol to give (E)-3,5-di-t-butyl-4-hydroxybenzophenone oxime as colorless needles.

Melting point: 162°–166° C.

NMR, $\delta_{CDCl_3}^{ppm}$: 1.36 (18H, s), 5.32 (1H), 7.24 (2H, s), 7.36 (5H, s).

IR, $\gamma_{KBr}^{cm-1}$: 3620, 3308, 2964, 1442, 1320, 1240, 1170, 970, 890, 776, 706, 676.

(c) The residue was recrystallized from dichloromethane/n-hexane to give (Z)-3,5-di-t-butyl-4-hydroxybenzophenone oxime as colorless prisms.

Melting point: 164°–167° C.

NMR, $\delta_{CDCl_3}^{ppm}$: 1.43 (18H, s), 5.24 (1H, s), 5.36 (1H), 7.15–7.55 (5H, m), 7.24 (2H, s).

IR, $\gamma_{KBr}^{cm-1}$: 3636, 3284, 2964, 2916, 1438, 1316, 1234, 1152, 936, 746, 736.

EXAMPLE 3

0.93 g of 3,5-di-t-butyl-4-hydroxybenzophenone oxime was dissolved in pyridine, and 0.28 g of acetyl chloride was added dropwise at room temperature. Thereafter, the mixture was stirred for 20 minutes. The reaction mixture was poured into ice water, extracted with benzene, washed with 4% HCl, water and a saturated aqueous solution of sodium bicarbonate, and dried. The solvent was distilled off, and the resulting crystals were recrystallized from ether/n-hexane to give 3,5-di-t-butyl-4-hydroxybenzophenone O-acetyloxime.

Melting point: 135.9°–136.7° C.

MMR, $\delta_{CDCl_3}^{ppm}$: 1.38, 1.41 (18H), 2.06, 2.14 (3H), 5.46 (1H, s), 7.16–7.60 (7H, m).

IR, $\gamma_{KBr}^{cm-1}$: 3560, 2960, 1760, 1440, 1205, 900, 780, 700.

EXAMPLE 4

3,5-di-t-butyl-4-hydroxybenzophenone oxime and propionyl chloride were treated in the same way as in Example 3 to obtain 3,5-di-t-butyl-4-hydroxybenzophenone O-propionyloxime.

Melting point: 131.7°–133.7° C. (recrystallized from ether/n-hexane).

NMR, $\delta_{CDCl_3}^{ppm}$: 1.14 (3H, t, J=8 Hz), 1.40 (18H, s), 2.38 (2H, q, J=8 Hz), 5.45 (1H, s), 7.14 (2H, s), 7.29–7.66 (5H, m).

IR, $\gamma_{KBr}^{cm-1}$: 3530, 2940, 1745, 1170, 690.

EXAMPLE 5

3,5-di-t-butyl-4-hydroxybenzophenone oxime and butyryl chloride were treated in the same way as in Example 3 to give 3,5-di-t-butyl-4-hydroxybenzophenone O-butyryloxime.

Melting point: 118.3°–119.3° C. (recrystallized from n-hexane).

NMR, $\delta_{CDCl_3}^{ppm}$: 0.89 (3H, t, J=8.0 Hz), 1.26 (2H, t, J=8.0 Hz), 1.26–1.78 (2H, m), 1.39, 1.42 (18H), 5.47 (1H, s), 7.15–7.65 (7H, m).

IR, $\gamma_{KBr}^{cm-1}$: 3540, 2950, 1755, 1430, 1080.

EXAMPLE 6

3,5-di-t-butyl-4-hydroxybenzophenone oxime and octanoyl chloride were treated in the same was as in Example 3 to give 3,5-di-t-butyl-4-hydroxybenzophenone O-octanoyloxime.

Melting point: 76.3°–77.2° C. (recrystallized from n-hexane).

NMR, $\delta_{CDCl_3}^{ppm}$: 0.88 (3H, t, J=8.0 Hz), 1.00–1.75 (10H, m), 1.38, 1.42 (18H), 2.28 (2H, t, J=8.0 Hz), 5.46 (1H, s), 7.14–7.65 (7H, m).

IR, $\gamma_{KBr}^{cm-1}$: 3580, 2950, 1770, 1435, 1240.

EXAMPLE 7

1.55 g of 3,5-di-t-butyl-4-hydroxybenzophenone and 0.5 g of hydrous hydrazine were dissolved in 15 ml of isopropanol, and after adding 0.2 ml of 47% hydrobromic acid, the solution was refluxed for 6 hours with stirring. After the reaction, isopropanol was distilled off under reduced pressure. The residue was dissolved in ethyl acetate, and washed with water. The organic layer was dried, and the solvent was distilled off under reduced pressure.

The resulting crystals were recrystallized from petroleum ether to give 3,5-di-t-butyl-4-hydroxybenzophenone hydrazone.

Melting point: 97.4°–116.8° C.

NMR, $\delta_{CDCl_3}^{ppm}$: 1.36, 1.44 (18H), 4.9 (2H), 5.2, 5.32 (1H), 7.01 (2H, s), 7.1–7.6 (5H, m).

IR, $\gamma_{KBr}^{cm-1}$: 3580, 3360, 2945, 1425, 1235, 770.

EXAMPLE 8

3,5-di-t-butyl-4-hydroxybenzophenone and acetohydrazide were treated in the same way as in Example 7 to give 3,5-di-t-butyl-4-hydroxybenzophenone acetylhydrazone.

Melting point: 205.2°–205.7° C. (recrystallized from dichloromethane/n-hexane)

NMR, $\delta_{(CD_3)_2SO}^{ppm}$: 1.30, 1.40 (18H), 2.28 (3H, s), 6.95 (2H, s), 7.1–7.6 (5H, m), 8.25 (1H).

IR, $\gamma_{KBr}^{cm-1}$: 3532, 3324, 2956, 1682, 1666, 1450, 1436, 1376, 1338, 1316, 1238, 1108, 558.

EXAMPLE 9

One gram of 3,5-di-t-butyl-4-hydroxybenzophenone was added to 2 ml of 1,1-dimethylhydrazine, and the mixture was heated at 70° to 75° C. for 8 hours in the presence of 20 mg of p-toluenesulfonic acid in autoclave. After cooling, the reaction mixture was poured into water and extracted with diethyl ether. The ethereal layer was washed with water and dried. The ether was distilled, and the residue was chromatographed on a silica gel column, and recrystallized from diethyl ether to give 3,5-di-t-butyl-4-hydroxybenzophenone dimethylhydrazone as pale yellow needles.

Melting point: 111°–124° C.

NMR, $\delta_{CDCl_3}^{ppm}$: 1.37, 1.4 (18H), 2.47, 2.51 (6H), 5.26 (1H), 7.18–7.69 (7H, m).

IR, $\gamma_{KBr}^{cm-1}$: 3625, 2950, 1440, 1310, 1240, 1155, 780, 710.

EXAMPLE 10

One gram of 3,5-di-t-butyl-4-hydroxybenzophenone and 880 mg of phenylhydrazine were refluxed under heating in 30 ml of benzene in the presence of 20 mg of p-toluenesulfonic acid for 3.5 hours. The reaction mixture was poured into water and extracted with benzene. The extract was chromatographed on a silica gel column, and recrystallized from diethyl ether/n-hexane to give 3,5-di-t-butyl-4-hydroxybenzophenone phenylhydrazone as colorless needles.

Melting point: 143.9°–144.8° C.

NMR, $\delta_{CDCl_3}^{ppm}$: 1.46 (18H, s), 5.48 (1H), 6.75–7.70 (12H, m), 7.60 (1H).

IR, $\gamma_{KBr}^{cm-1}$: 3620, 3320, 2964, 1600, 1504, 1434, 1246, 1236, 1130, 694.

EXAMPLE 11

1.60 g of 3,5-di-t-butyl-4-hydroxybenzophenone and 0.67 g of semicarbazide hydrochloride were dissolved in 12 ml of pyridine, and the solution was refluxed for 6 hours. After the reaction, ethyl acetate was added to the reaction mixture, and the mixture was washed with 5% hydrochloric acid and water and dried. The solvent was removed by concentration, and the residue was chromatographed on a silica gel column and recrystallized from diethyl ether to give 3,5-di-t-butyl-4-hydroxybenzophenone semicarbazone.

Melting point: 241.1°–243.0° C.

NMR, $\delta_{(CD_3)_2SO}^{ppm}$: 1.39 (18H, s), 3.29 (3H, s), 6.68–7.41 (7H, m), 9.05 (1H).

IR, $\gamma_{KBr}^{cm-1}$: 3632, 3356, 2960, 1704, 1506.

EXAMPLE 12

6.2 g of 3,5-di-t-butyl-4-hydroxybenzophenone and 2.2 g of thiosemicarbazide were dissolved in 20 ml of toluene, and 0.4 g of p-toluenesulfonic acid was added. The solution was refluxed for 16 hours while removing water. After the reaction, dilute hydrochloric acid was added, and the mixture was extracted with ethyl acetate. The organic layer was washed with water and dried, and the solvent was distilled off under reduced pressure. The residue was chromatographed on a silica gel column, and recrystallized from dichloromethane/n-hexane to give 3,5-di-t-butyl-4-hydroxybenzophenone thiosemicarbazone.

Melting point: 215.8°–217.8° C. (decomposed).

NMR, $\delta_{(CD_3)_2SO}^{ppm}$: 1.32, 1.42 (18H), 3.27 (1H), 6.98 (2H, s), 7.2–8.0 (5H, m), 8.3 (1H), 8.53 (2H).

IR, $\gamma_{KBr}^{cm-1}$: 3436, 3356, 3244, 1606, 1486, 1472, 1436, 468.

The following are examples of formulating drugs containing the compounds of formula (I) provided by this invention.

FORMULATION EXAMPLE A

| | mg/capsule |
|---|---|
| Recipe 1-a for 50 mg capsules | |
| Active ingredient | 50 |
| Starch | 30 |
| Lactose | 27.8 |
| Magnesium stearate | 2.2 |
| | 110 mg |

-continued

|  | mg/capsule |
| --- | --- |
| Recipe 1-b for 100 mg capsules | |
| Active ingredient | 100 |
| Starch | 60 |
| Lactose | 55.6 |
| Magnesium stearate | 4.4 |
|  | 220 mg |

The active ingredient was well crushed, and mixed with starch, lactose and magnesium stearate. After thorough mixing, the mixture was filled in capsules.

What is claimed is:

1. A compound represented by the formula

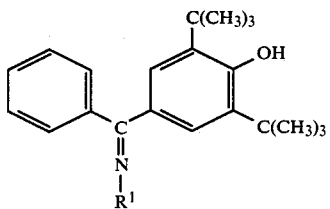

wherein $R^1$ represents a hydroxyl group, an alkanoyloxy group or a group of the formula

in which $R^2$ represents a hydrogen atom or a lower alkyl group, and $R^3$ represents a hydrogen atom, a lower alkyl group, an alkanoyl group, a phenyl group, a carbamoyl group or a thiocarbamoyl group, or a salt thereof.

2. The compound of claim 1 wherein $R^1$ represents a hydroxyl group, an alkanoyloxy group or an amino group.

3. The compound of claim 1 which is 3,5-di-t-butyl-4-hydroxybenzophenone oxime or 3,5-di-t-butyl-4-hydroxybenzophenone O-propionyloxime.

4. An anti-inflammatory, analgesic or anti-rheumatic composition comprising an effective amount for the purpose intended of a compound of claim 1 or its pharmaceutically acceptable salt and a pharmaceutically acceptable carrier or diluent.

5. A method for treating inflammation in mammals, which comprises administering to the mammal an anti-inflammatory effective amount of a compound of claim 1 or its pharmaceutically acceptable salt.

6. A method for treating pain in mammals, which comprises administering to the mammals an analgesically effective amount of a compound of claim 1 or its pharmaceutically acceptable salt.

7. A method for treating rheumatism in mammals, which comprises administering to the mammals an anti-rheumatically effective amount of a compound of claim 1 or its pharmaceutically acceptable salt.

* * * * *